Dec. 11, 1934. J. G. LAYTON Plant Pat. 115
HYBRID TEA ROSE
Filed July 15, 1933
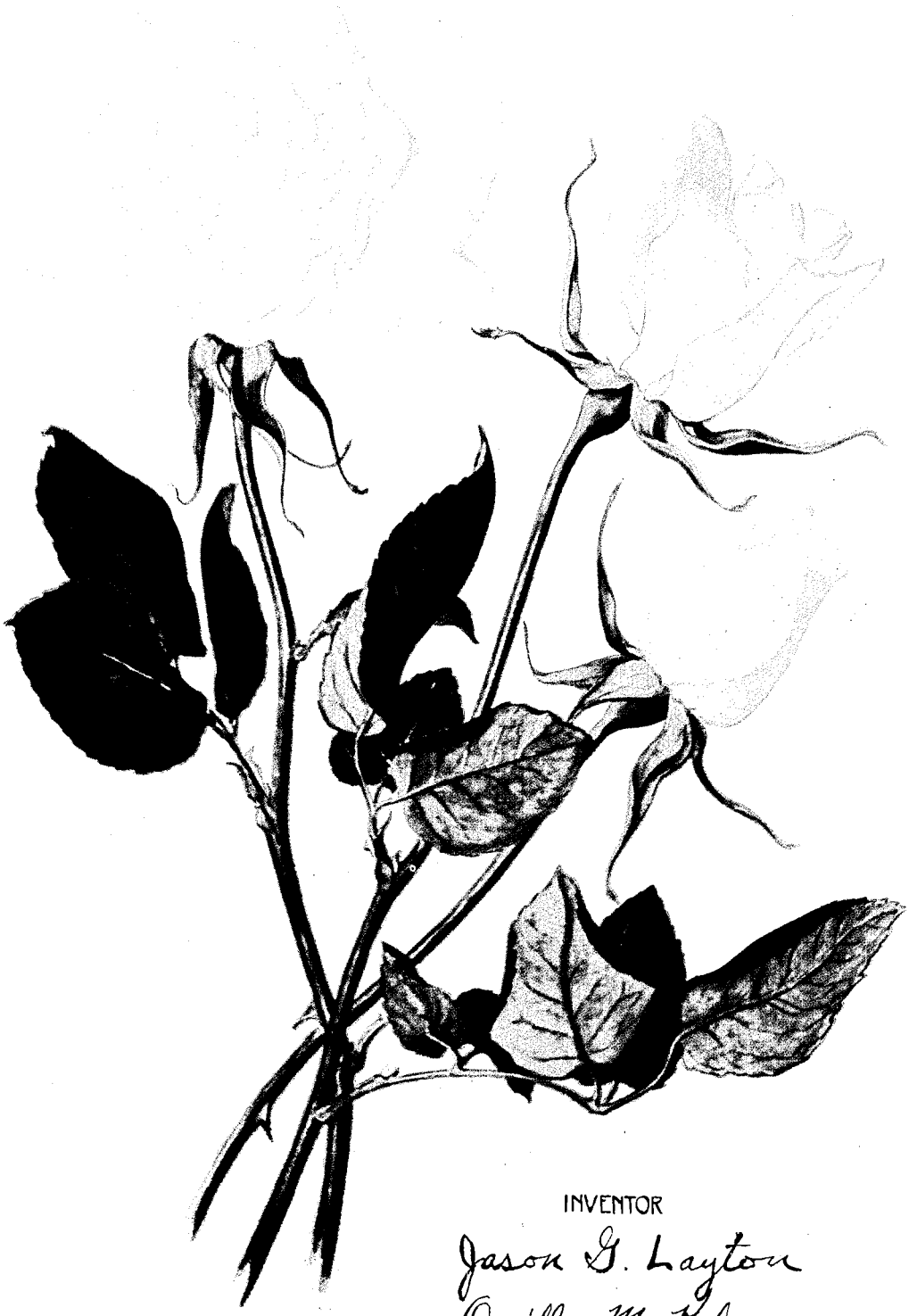
INVENTOR
Jason G. Layton
By Orville M. Kile
PLANT PATENT AGENT Patented Dec. 11, 1934

Plant Pat. 115

UNITED STATES PATENT OFFICE

115

HYBRID TEA ROSE

Jason G. Layton, Olean, N. Y.

Application July 15, 1933, Serial No. 680,629

1 Claim. (Cl. 47—61)

My present invention relates to improvements in yellow or amber hybrid tea roses. The objects of these improvements are, briefly stated, to provide a rose of the type mentioned having new and pleasing color tones, large size, full petallage, notable resistance to disease, and being a prolific producer and easily propagated.

My new rose originated as a bud sport of the well known variety Joanna Hill. I have carefully tested and propagated it in order to prove its superior qualities and it was accepted by the American Rose Society as a new variety in 1932.

The accompanying illustration shows in full color a typical bud, half opened and fully opened flowers, and foliage—all depicted as nearly true to life as possible.

The following is a detailed description of this rose plant and flower.

*The bush or plant* under ordinary greenhouse conditions grows 4 to 4½ feet in height. It grafts readily on Manetti stock and is easily budded giving a high percentage of starts. It has always been free from black spot and mildew under both greenhouse and outside conditions. The plant has the ability to get back into production quickly after heavy cropping and lends itself well to strong forcing to produce large crops for any given day.

*Stem*—medium size, inclined to the zig-zag rather than entirely straight; "forest green" in color (Plate XVII Ridgway's Color Standard and Nomenclature); completely free of spines and no thorns occur above the second or third leaf branch. The first leaves are found 2½ to 3 inches below the blossom. The thorns are rather large, pinkish in color with white points and fairly numerous at a point 8 to 10 inches below the flower.

*Leaves*—on flower-bearing stems are 2½ to 3 inches long, broad rather than slender in form, and the petioles bear 1 to 3 rather prominent thorns on the third and lower leaf branches below the flower. Leaves are smooth but not glossy, "dark green" in color (Plate XVIII Ridgway's Color Standard and Nomenclature), and have a tendency to roll at the edges. The leaves are minutely but not prominently serrated. Leaf branches on the flower stem consist of either 3 or 5 separate leaves; those leaves back of the tip leaf stand at an acute angle to the plane of the tip leaf, giving a "winged" effect.

*Stipules*—are of medium size, sharp pointed, with many hairs on the edges.

*Sepals*—five in number, relatively short, wide at the base and tapering evenly to a point, with no tendency to foliaceous development.

*Hips*—rather large and long, particularly long in that part from the point of attachment to the flower to the point where tapering begins.

*Buds*—long and of good size, pointed at first then somewhat urn-shaped.

*Flowers*—very fragrant, large, in the month of May measuring 4 to 5 inches across the top when fully opened, and numbering approximately 17 large obovate petals constituting the outer whorls, 12 medium-sized rounded petals making up the outside of the ball-like effect in the center of the flower, and 30 small petals at the center. These latter petals are irregular and crinkled in form and some of them seem to be borne on filaments similar to the stamens—probably modified anthers.

So numerous and so overlapping are these central small petals that the stamens or stigmas are not exposed to view.

The outer three or four rows of petals progressively roll into pointed and usually triangular forms as the blossom opens.

The veining of the petals is not so distinct as to be noticeable in the ordinary viewing of the flower.

The stamens are numerous, long, buff in color, and mounted by exceptionally large flat anthers. The stigmas are also numerous, pink to reddish in color and topped by a whitish granular substance.

*Color*—The half-opened flower is approximately "straw yellow" (Plate XVI) on the outer edges of the petals, with deeper color approaching "maize yellow" to "buff yellow" (Plate IV) toward the base of the petals. The color effect of all the central portion of the flower is approximately "amber-yellow" (Plate XVI).

All the color tones become lighter as the blossom matures.

The blossom passes through three distinct form phases and is long lasting. First the opening bud has a decided urn shape, with the outer row of petals curling outward moderately at the top; next the outer rows of petals open and leave a pointed amber-yellow center, then the remaining petals forming the pointed center open and expose the numerous small petals in the center and in this latter stage the larger outer and central petals all curl back into pointed triangular forms.

The chief characters which, either separately or in combination, distinguish my new variety from all other known varieties of roses are:

1. Colors of buds and blossoms as described above.

2. Flower stems free of spines and thorns for a distance of 7 or 8 inches below the blossom, but having rather numerous thorns below that point.

3. Leaves of the shape and color noted and set at an unusual angle to the leaf branch stem as described.

4. The opening habits of the blossom and the rolling of the petals, together with the large number of petals and their sizes and shapes as described.

5. The non-foliaceous sepals and unusual form of hips.

6. Great abundance and large size of sex organs.

7. Superior producing and keeping qualities, also ease of propagation and freedom from disease.

Having thus disclosed my invention I claim:

A variety of rose as herein shown and described, characterized chiefly by its straw-yellow and amber-yellow colors, its full petallage, thornless upper stem, luxuriant dark green foliage, notable fragrance and superior growing and shipping qualities and freedom from disease.

JASON G. LAYTON.